United States Patent [19]

Gramlich et al.

[11] Patent Number: 4,707,302

[45] Date of Patent: Nov. 17, 1987

[54] 2-SUBSTITUTED 4,4,7,7-TETRAMETHYL-1,3-DIOXACY-CLOHEPTANES, PREPARATION AND USE THEREOF AS SCENTS

[75] Inventors: Walter Gramlich, Edingen-Neckarhausen; Hardo Siegel, Speyer, both of Fed. Rep. of Germany

[73] Assignee: BASF Aktiengesellschaft, Ludwigshafen, Fed. Rep. of Germany

[21] Appl. No.: 10,420

[22] Filed: Feb. 3, 1987

[30] Foreign Application Priority Data

Feb. 6, 1986 [DE] Fed. Rep. of Germany ....... 3603661

[51] Int. Cl.$^4$ ............................ A61K 7/46; C11B 9/00; C07C 43/18
[52] U.S. Cl. ........................................ 512/11; 568/670; 568/671
[58] Field of Search ........................ 568/670, 672; 252/522 R

[56] References Cited

U.S. PATENT DOCUMENTS

| | | | |
|---|---|---|---|
| 3,122,562 | 2/1964 | Sterling et al. | 568/670 |
| 3,966,768 | 6/1976 | Pawloski | 568/670 |
| 4,294,727 | 10/1981 | Conrad et al. | 252/522 |

FOREIGN PATENT DOCUMENTS 0024473 6/1984 European Pat. Off. ............ 568/670

OTHER PUBLICATIONS

Chemical Abstracts, Band 86, No. 13, 28 Mar. 1977, Seite 410, Spaltent 1-2, Zusammenfassungsnr., 95863w, Columbus, Ohio, US.
Chemical Abstracts, Band 86, No. 15, 11 Apr. 1977, Seite 293, Spalte 2, Zusammenfassungsnr., 111086c, Columbus, Ohio, US.
"J. Amer. Chem. Soc.", 103 (1981), pp. 936-938, Savriol-Lord et al.
Bull. Soc. Chim. FR. (1975), pp. 1763-1766, Soulier et al.
J. Org. Chem., vol. 40, No. 4 (1975), pp. 450-453, Gianni et al.
CA 69:P19996a, Jennings et al, "Chem. Abs.", vol. 69, P1996a.
Houben-Weyl Methoden der Orpanischen Chemie, Bana VI 13 (1965), pp. 204-213.

*Primary Examiner*—Werren B. Lone
*Attorney, Agent, or Firm*—Oblon, Fisher, Spivak, McClelland, & Maier

[57] ABSTRACT

2-Substituted 4,4,7,7-tetramethyl-1,3-dioxacycloheptanes of the general formula I

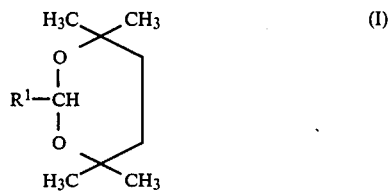

where $R^1$ is a straight-chain or branched alkyl of 1 to 10 carbon atoms which additionally may contain oxygen in the form of an ether group or is 5- to 8-membered cycloalkyl of up to 10 carbon atoms which may additionally contain oxygen in the form of an ether group, of which particularly interesting representatives are 2,4,4,7,7-pentamethyl-1,3-dioxacycloheptane, 2-tert.-butyl-4,4,7,7-tetramethyl-1,3-dioxacycloheptane and 2-isopropyl-4,4,7,7-tetramethyl-1,3-dioxacycloheptane, are prepared and used as scents.

5 Claims, No Drawings

2-SUBSTITUTED 4,4,7,7-TETRAMETHYL-1,3-DIOXACYCLOHEPTANES, PREPARATION AND USE THEREOF AS SCENTS

The present invention relates to 2-substituted 4,4,7,7-tetramethyl-1,3-dioxacylcloheptanes of the general formula I

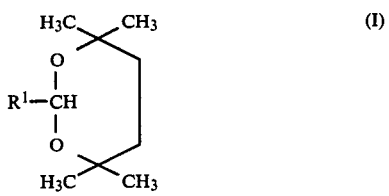

where $R^1$ is straight-chain or branched alkyl of 1 to 10 carbon atoms which may additionally contain oxygen in the form of an ether group, or is 5- to 8-membered cycloalkyl of up to 10 carbon atoms which may additionally contain oxygen in the form of an ether group, to the preparation thereof and to the use thereof as scents.

Owing to the fact that the availability of many natural scent components is unreliable, being dependent on many imponderables, and given the need to match changing fashions in taste, the scent industry constantly requires new scents which, either on their own or in the form of compositions, are useful perfumes having interesting fragrance notes. In addition, there is an ever-growing trend toward perfuming products of everyday life, such as cosmetics and industrial articles such as glues, detergents and cleaners, for household sprays and the like.

Since, owing to the lack of knowledge about the relationship between structure and olfactory properties, a specific synthesis of scents having a desired scent quality is not possible, it is an object of the present invention to find compounds which have been useful scent properties.

We have found that this object is achieved with the above-described compounds of the formula I, which are very interesting scents.

Structurally related compounds of the type of substituted dioxacylcloheptanes have hitherto been usually discussed in connection with theoretical studies, such as conformation studies (cf. T. B. Grindley et al., J. Amer. Chem. Soc. 103 (1981), 936–938).

2-Monoalkylated or 2-dialkylated 4,7-dihydro-1,3-dioxepines (1,3-dioxa-5-cyclohexenes) of the formula IV

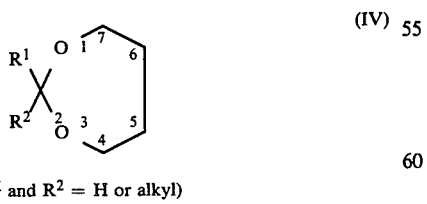

($R^1$ and $R^2$ = H or alkyl)

are known from the literature (see M. J. Soulier et al., Bull. Soc. Chim. Fr. 1975, 1763–66) as herbicides and polymerization catalysts and also as intermediates for scents (see European Pat. No. 24,473). They themselves have no interesting olfactory properties and in none of the references mentioned are they mentioned as scents.

In addition, 4,7-dimethyl-4,7-dihydro-1,3-dioxepine and 2-tert.-butyl-4,7-dimethyl-4,7-dihydro-1,3-dioxepine are known from a paper about confirmation analyses in J. Org. Chem. 40, 4 (1975), 450–453. This paper does not say anything about possible scent qualities.

Moreover, 2-unsubstituted 4,4,7,7-tetramethyl-4,7-dihydro-1,3-dioxepine and 4,7-dimethyl-4,7-diethyl-4,7-dihydro-1,3-dioxepine are known from CA69:P19996a as a component for preparing copolymers. These last-mentioned references likewise provide no indication whatsoever that compounds having the 1,3-dioxepine structure could be of interest for use as scents.

It was therefore very surprising that the 2-substituted 4,4,7,7-tetramethyl-1,3-dioxacycloheptanes of the invention are compounds having very interesting scent notes and therefore can be used as scents.

The present invention therefore also relates to the use of the compounds of the general formula I as scents and scent compositions which contain from 1 to 50% by weight of 2-substituted 4,4,7,7-tetramethyl-1,3-dioxacycloheptanes of the formula I.

The present invention further relates to a process for preparing the 2-substituted 4,4,7,7-tetramethyl-1,3-dioxacycloheptane of the general formula I claimed in claim 1 which comprises reacting an aldehyde of the general formula II

where $R^1$ is as defined in claim 1, in a manner known per se with 2,5-dimethylhexane-2,5-diol of the formula III

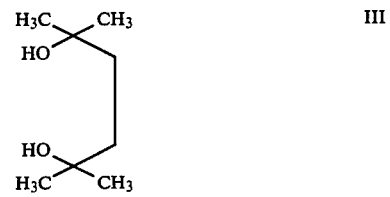

and to a process for preparing 2-substituted 4,4,7,7-tetramethyl-1,3-dioxacycloheptanes of the general formula I as claimed in claim 1, which comprises hydrogenating the corresponding novel 2-substituted 4,4,7,7-tetramethyl-1,3-dioxa-5-cycloheptenes of the general formula IV

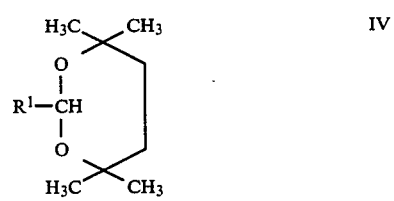

in a manner known per se.

The reaction of aldehyde II with III is effected using a cyclization method described in the literature, so that no details need be given (see Houben-Weyl, Methoden der organischen Chemie, volume VI/3 (1965), pages 204 et seq.). It is advantageous to use a cyclization catalyst, such as p-toluenesulfonic acid, phosphoric acid or an acid ion exchanger, and an entraining agent, such as toluene or cyclohexane, to remove the water which forms in the course of the cyclization.

Suitable aldehydes of the formula II are for example acetaldehyde, propionaldehyde, 2-methylpropanal, n-butyraldehyde, 2-methylbutanal, 3-methylbutanal, 2-ethylbutanal, n-valeraldehyde, 2-methylpentanal, 3-methylpentanal, 4-methylpentanal, 2,2-dimethylpropanal (pivalaldehyde), 2,2-dimethylbutanal or 2,2-dimethylpentanal. For even unsubstituted higher aldehydes, such as n-hexanal, n-heptanal, n-octanal, n-nonanal, decanal and monoalkylated or polyalkylated derivatives thereof can be used. The best known representatives are the chemical large-scale product 2-ethylhexanal and 3,5,5-trimethylhexanal.

Suitable cyclic aldehydes are for example cyclopentylcarbaldehyde and cyclohanecarbaldehyde, and suitable oxygen-containing representatives are for example methoxyacetaldehyde and tetrahydropyran-3-carbaldehyde.

2,5-Dimethylhexane-2,5-diol is a commercially available important industrial intermediate.

Suitable catalysts for the hydrogenation of the novel 1,3-dioxa-5-cycloheptenes of the formula IV are all the catalysts suitable for the hydrogenation of C—C double bonds, such as palladium on various carriers (active carbon, aluminum oxide, titanium dioxide), Raney nickel, and ruthenium or platinum on various carriers.

The hydrogen pressures required depend on the catalyst used and on the proportion by weight thereof. Dehydrogenation is problem-free, since no hydrogenable functional groups are present in the molecule. For further details concerning such hydrogenations, see Houbenweyl, Methoden der organischen Chemie, volume IV/1c (1980), pages 145 et seq. Normally, however, the direct cyclization starting from the inexpensive dimethylhexanediol will be employed for synthesizing the novel compounds.

The novel 4,4,7,7-tetramethyl-1,3-dioxacycloheptanes of the formula I combine well with other scents in various mixing ratios to give novel and interesting scent compositions.

In addition to their use in fine perfumes, compositions of this type can be used for perfuming cosmetics such as creams, lotions, aerosols or toilet soaps, industrial products such as cleaners and detergents, fabric softeners, disinfectants and textile treatment agents.

The novel compounds are distinguished in particular by their note of freshness and therefore can markedly enhance existing compositions. Since, in addition to the acetal group, they have no further functional group, they are very stable in neutral and alkaline media.

Particularly useful compounds as scents for fine perfumes are:
2-tert.-Butyl-4,4,7,7-tetramethyl-1,3-dioxacycloheptane, 2,4,4,7,7-pentamethyl-1,3-dioxacycloheptane and 2-isopropyl-4,4,7,7-tetramethyl-1,3-dioxacycloheptane.

The following Examples illustrate the subject matter of the invention in more detail.

EXAMPLE 1

2-tert.-Butyl-4,4,7,7-tetramethyl-1,3-dioxacycloheptane

A mixture of 730 g (5 mol) of 2,5-dimethylhexane-2,5-diol, 3 g of p-toluenesulfonic acid, 430 g (5 mol) of pivalaldehyde and 1 l of toluene was refluxed for 4 hours (h) during which the water of reaction produced (90 ml) was removed. The reaction mixture was then cooled down to room temperature (RT) and stirred up with 10 ml of 25% strength aqueous sodium hydroxide solution, the phases were separated, the organic phase was washed with a little water until neutral, and the toluene was then removed at 50°–60° C. The residue obtained was fractionated under reduced pressure affording 909 g (4.25 mol) of 2-tert.-butyl-4,4,7,7,-tetramethyl-1,3-dioxacycloheptane (boiling point 54° C./0.2 mbar). This corresponds to a yield of 85% of theory.

EXAMPLE 2

2-Isopropyl-4,4,7,7-tetramethyl-1,3-dioxacycloheptane

In a 300 ml autoclave, a mixture of 60 g of 2-isopropyl-4,4,7,7-tetramethyl-1,3-dioxa-5-cycloheptene, 70 ml of ethyl acetate and 10 g of an 0.5% palladium-/aluminum oxide catalyst was hydrogenated at 150° C. and 150 bar of hydrogen pressure.

The catalyst and the ethyl acetate were removed, and 52 g of 2-isopropyl-4,4,7,7-tetramethyl-1,3-dioxacycloheptane having a boiling point of 77° C./23 mbar were obtained by distillation.

The physical properties of the compounds prepared in Examples 1 and 2 and of other olfactorily interesting novel compounds of the formula I prepared analogously to Example 1 are shown in the Table below.

TABLE

| No. | | -4,4,7,7-tetramethyl-1,3-dioxacycloheptane | Boiling point [°C./mbar] | $n_D^{25}$ | Description of scent |
|---|---|---|---|---|---|
| 1 | Pivalaldehyde | 2-tert.-butyl- | 54/0.2 | 1.4338 | very intensive and fresh green note (rose, maybells), civet |
| 2 | Isobutyraldehyde | 2-isopropyl- | 77/23 | 1.4337 | fresh intensive note, clarylike |
| 3 | Acetaldehyde | 2-methyl- | 68/26 | 1.4310 | strong camphor note, cooling effect, intensive, fresh |
| 4 | Propanal | 2-ethyl- | 74/22 | 1.4333 | fresh herbacaeous/fruity note, methylchavicol like |
| 5 | Butanal | 2-propyl- | 88/24 | 1.4362 | fresh fruity note |
| 6 | Pentanal | 2-butyl- | 50/0.3 | 1.4386 | herbacaeous green note |
| 7 | 3-Methylbutanal | 2-(2-methylpropyl) | 27/0.2 | 1.4367 | herbacaeous mint note |
| 8 | 2-Methylpentanal | 2-(1-methylbutyl) | 63/0.2 | 1.4401 | weak herbacaeous note |
| 9 | Cyclopentylcarbaldehyde | 2-cyclopentyl | 48/0.03 | 1.4595 | herbacaeous note, celerylike |
| 10 | Methoxyacetaldehyde | 2-methoxymethyl | 98/42 | 1.4382 | fresh mint note, green, floral |

APPLICATION EXAMPLE

The large number of ways of using the novel compounds will now be indicated by demonstrating the effect of 2-tert.-butyl-4,4,7,7-tetramethyl-1,3-dioxacycloheptane on a floral fantasy composition A (cf. G. Ohloff, H. Rode-Gowal in Kosmetika, Riechstoffe und Lebensmittelzusatzstoffe, Georg Thieme Verlag, Stuttgart 1978, page 61).

| Components | Composition A [proportion] | Composition B [proportion] |
| --- | --- | --- |
| Hydroxycitronellal | 100 | 0 |
| 2-tert.-Butyl-4,4,7,7-tetra-methyl-1,3-dioxacycloheptane | 0 | 100 |
| 2-Phenylethanol | 50 | 50 |
| Ylang (synthetic) | 100 | 100 |
| Indan musk | 20 | 20 |
| Coumarin | 80 | 80 |
| Linalool | 200 | 200 |
| Linalyl acetate | 150 | 150 |
| Benzyl acetate | 50 | 50 |
| Bergamot (synthetic) | 50 | 50 |
| Mixture of 1-(3,4-epoxy-4-methylpentyl)-4- and -5-formylcyclohexene | 100 | 100 |
|  | 1,000 | 1,000 |

The replacement of the hydroxycitronnellal in composition A by 2-tert.-butyl-1,3-dioxacycloheptane leads to composition B, which has a significantly fresher and much more natural overall note.

We claim:
1. A 2-substituted 4,4,7,7-tetramethyl-1,3-dioxacycloheptane of the general formula I

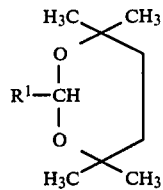

where $R^1$ is a straight-chain or branched alkyl of 1 to 10 carbon atoms which additionally may contain oxygen in the form of an ether group or is 5- to 8-membered cycloalkyl of up to 10 carbon atoms which may additionally contain oxygen in the form of an ether group.

2. 2,4,4,7,7-Pentamethyl-1,3-dioxacycloheptane.
3. 2-tert.-Butyl-4,4,7,7-tetramethyl-1,3-dioxacycloheptane.
4. 2-Isopropyl-4,4,7,7-tetramethyl-1,3-dioxacycloheptane.
5. A scent composition which contains from 1 to 50% by weight of a 2-substituted 4,4,7,7-tetramethyl-1,3-dioxacycloheptane of the general formula I as claimed in claim 1.

* * * * *